United States Patent [19]

Nakamura et al.

[11] Patent Number: 4,943,528
[45] Date of Patent: Jul. 24, 1990

[54] PROCESS FOR THE PRODUCTION OF OPTICALLY ACTIVE (R)-(−)-3-HALO-1,2-PROPANEDIOL

[75] Inventors: Tetsuji Nakamura; Ichiro Watanabe, both of Kanagawa, Japan

[73] Assignee: Nitto Chemical Industry Co., Ltd., Tokyo, Japan

[21] Appl. No.: 438,124

[22] Filed: Nov. 20, 1989

[30] Foreign Application Priority Data

Nov. 22, 1988 [JP] Japan ................................. 63-293615
Apr. 21, 1989 [JP] Japan ................................. 1-100173

[51] Int. Cl.$^5$ ................................................ C12P 7/18
[52] U.S. Cl. ..................................... 435/158; 435/280
[58] Field of Search ............................... 435/158, 280

[56] References Cited

PUBLICATIONS

Takahashi et al—Chem. Abst., vol. 108 (1988), p. 166,128w.

*Primary Examiner*—Sam Rosen
*Attorney, Agent, or Firm*—Sughrue, Mion, Zinn, Macpeak & Seas

[57] ABSTRACT

A process for the production of an optically active (R)-(−)-3-halo-1,2-propanediol which comprises contacting a 1,3-dihalo-2-propanol with a dehalogenase originating from a microorganism belonging to the genus Corynebacterium or Microbacterium. This process makes it possible to produce the (R)-(−)-3-halo-1,2-propanediol, which is highly useful as a starting material in the synthesis of various drugs and physiologically active substances, theoretically at a yield of 100%.

2 Claims, No Drawings

PROCESS FOR THE PRODUCTION OF OPTICALLY ACTIVE (R)-(−)-3-HALO-1,2-PROPANEDIOL

FIELD OF THE INVENTION

This invention relates to a process for the production of an optically active (R)-(−)-3-halo-1,2-propanediol. It is known that (R)-(−)-3-halo-1,2-propanediol is useful as a starting material for synthesizing, for example, various drugs and physiologically active substances such as L-carnitine (cf. JP-A-57-165352 (the term "JP-A" as used herein means an "unexamined published Japanese patent application").

BACKGROUND OF THE INVENTION

Known methods for the production of an optically active (R)-(−)-3-halo-1,2-propanediol include one wherein D-mannitol is used as a starting material (cf. JP-A-57-165352, and U.S. Pat. No. 4,413,142) and another one wherein methyl-5-chloro-5-deoxy-α-L-arabinofranocide is used as a starting material [cf. *Chemistry and Industry*, p. 535, 15, July (1978)]. However, each of these chemical synthesis methods requires a complicated procedure, which causes some problems when it is to be applied on an industrial scale. On the other hand, there are reported some biological methods for the production of (R)-(−)-3-halo-1,2-propanediol, for example, one wherein a racemic mixture of (R,S)-3-halo-1,2-propanediol is treated with a microorganism which selectively metabolizes (S)-(+)-3-halo-1,2-propanediol to thereby obtain the desired (R)-(−)-3-halo-1,2-propanediol as the residue (cf. JP-A-62-158494) and another one wherein a racemic mixture of (R,S)-2,3-dichloro-1-propanol is treated with a bacterium belonging to the genus Pseudomonas having (R)-(+)-2,3-dichloro-1-propanol metabolizing activity to thereby obtain the desired (R)-(−)-3-chloro-1,2-propanediol (cf. JP-A-62-69993). However, each of these methods, wherein, a racemic mixture is used as a starting material, gives a yield of the (R)-(−)-3-halo-1,2-propanediol, based on the starting material, of 50% or below. Thus, the methods are disadvantageous from an economical point of view.

SUMMARY OF THE INVENTION

Under these circumstances, we have conducted extensive studies in order to establish a process for the production of an optically active (R)-(−)-3-halo-1,2-propanediol on an industrial scale. As a result, we have found out that an optically active (R)-(−)-3-halo-1,2-propanediol can be readily obtained from a 1,3-dihalo-2-propanol, which is an inexpensive prochiral compound, by using a dehalogenase originating from a microorganism, which had been isolated from soil by us, thus completing the present invention.

Accordingly, the present invention provides a process for the production of an optically active (R)-(−)-3-halo-1,2-propanediol which comprises contacting a 1,3-dihalo-2-propanol with a dehalogenase.

According to the present invention, it is theoretically possible to obtain the target compound at a yield of 100%, since a prochiral substrate is used therein.

It has not been known until now to carry out the above-described stereospecific dehalogenation reaction by utilizing the action of an enzyme originating from a microorganism. Thus findings have been first attained by the present inventors.

DETAILED DESCRIPTION OF THE INVENTION

The dehalogenase to be used in the present invention is an enzyme which can convert a halogen atom in a 1,3-dihalo-2-propanol into a hydroxyl group. Particular examples thereof include enzymes produced by the N-653 and N-1074 strains belonging to the genus Corynebacterium and one produced by the N-4701 strain belonging to the genus Microbacterium, each isolated and found by us for the first time. These microorganisms have been deposited with the Fermentation Research Institute, Agency of Industrial Science and Technology under the deposit number FERM P-10390 (Corynebacterium sp. N-653), after conversion to deposition under the Budapest Treaty, FERM BP-2642; FERM P-10391 (Corynebacterium sp. N-1074), after conversion to deposition under the Budapest Treaty, FERM BP-2643; and FERM P-10674 (Microbacterium sp. N-4701), after conversion to deposition under the Budapest Treaty, FERM BP-2644, respectively The mycological properties of these strains are as follows.

N-653
Morphology: polymorphic bacillus.
Colony-peripheral cell: showing no extension.
Gram stain: +.
Acid-fastness: −.
Spore: not observed.
Motility: +.
Oxidase: −.
Catalase: +.
O-F test: oxydative.
Growth under anaerobic conditions: −.
Presence of meso-diaminopimelic acid in hydrochloric acid hydrolyzate of the whole cell: −.
Diamino acid in cell wall: diaminobutyric acid.
Glycolyl test: −(acetyl-type).
Digestion of starch: −.
Liquefying of gelatin: +.
Digestion of cellulose: −.
Digestion of urea: −.
Heat stability in skim milk medium: 30 minutes at 63° C.: −; 15 minutes at 72° C.: −.

N-1074
Morphology: polymorphic bacillus.
Colony-peripheral cell: showing no extension.
Gram stain: +.
Acid-fastness: −.
Spore: not observed.
Motility: +.
Oxidase: −.
Catalase: +.
O-F test: oxydative.
Growth under anaerobic conditions: −.
Presence of meso-diaminopimelic acid in hydrochloric acid hydrolyzate of the whole cell: −.
Diamino acid in cell wall: diaminobutyric acid.
Glycolyl test: −(acetyl-type).
Digestion of starch: +.
Liquefying of gelatin: −.
Digestion of cellulose: −.
Digestion of urea: −.
Heat stability in skim milk medium: 30 minutes at 63° C.: −; 15 minutes at 72° C.: −.

N-4701
Morphology: polymorphic bacillus.

Colony-peripheral cell: showing no extension.
Gram stain: +.
Spore: not observed.
Motility: +.
Flagellum: polar to side.
Colony color: yellowish orange.
Oxidase: +.
Catalase: +.
O-F test: oxydative.
Growth under anaerobic conditions: —.
Presence of meso-diaminopimelic acid in hydrochloric acid hydrolyzate of the whole cell: —.
Diamino acid in cell wall: lysine.
Glycolyl test: +(glycolyl-type).
Digestion of starch: +.
Liquefying of gelatin: —.
Reduction of nitrate: —.
Utilization of arginine: +.
Production of Hydrogen sulfide: —.
Digestion of urea: —.
Heat stability in skim milk medium: 30 minutes at 60° C.: —;
Production of acid:
  inulin: +.
  glycerol: —.
  glucose: +.
  sucrose: +.
  trehalose: +.
  raffinose: +.

Based on these mycological properties, the N-653 and N-1074 strains have been identified as bacteria belonging to the genus Corynebacterium while the N-4701 strain has been identified as one belonging to the genus Microbacterium, according to Bergey's Manual of Systematic Bacteriology, vol. 2 (1986).

These microorganisms may be cultured in any common medium in which such microorganisms can grow. For example, the medium may contain a carbon source selected from among saccharides such as glucose, fructose, sucrose and maltose, organic acids such as acetic and citric acids and alcohols such as ethanol and glycerol; a nitrogen source selected from among common natural nitrogen sources such as peptone, meat extract, yeast extract, protein hydrolyzates and amino acids and ammonium salts of various inorganic and organic acids optionally together with inorganic salts, trace metal salts and vitamins. Furthermore, it is useful to add, for example, 1,3-dichloro-2-propanol or 3-chloro-1,2-propanediol to the medium in order to induce a high enzymatic activity.

These microorganisms may be cultured in a conventional manner. For example, they may be aerobically cultured at a pH value of from 4 to 10 and at a temperature of from 20° to 40° C. for 10 to 96 hours.

Examples of the 1,3-dihalo-2-propanol to be used in the present invention are 1,3-dichloro-2-propanol and 1,3-dibromo-2-propanol.

The 1,3-dihalo-2-propanol may be treated with the dehalogenase to thereby give the desired (R)-(—)-3-halo-1,2-propanediol in the following manner. When said dehalogenase originates from a microorganism, the substrate may be added to the culture liquor of the microorganism thus obtained or a cell suspension obtained by, for example, centrifuging the same. Alternately, the substrate may be added to a suspension of a processed cell material (e.g., ground cells or a cell extract such as a crude or purified enzyme) or a suspension of cells immobilized in a conventional manner or the processed cell material thereof. Furthermore, the substrate may be added to the culture medium upon the culture of the microorganism so as to conduct the reaction as the culture proceeds.

The concentration of the substrate in the reaction mixture preferably ranges from about 0.1 to 10% (w/v), though it is not restricted thereby. The substrate may be added to the reaction mixture either at once or by portions.

The reaction may be preferably conducted at a temperature of from 5 to 50° C., more preferably 10 to 35° C., and at a pH value of from 4 to 10, more preferably 6 to 9.

Although the reaction period may vary depending on the concentration of the substrate, the concentration of the cells and other factors, it is preferable to control the reaction conditions in such a manner so as to complete the reaction within about 1 to 120 hours.

The (R)-(—)-3-halo-1,2-propanediol thus formed and accumulated in the reaction mixture may be recovered and purified by a known method. For example, the cells are removed from the reaction mixture and then extracted with a solvent such as ethyl acetate. Then, the solvent is distilled off under reduced pressure to thereby give a syrup of the (R)-(—)-3-halo-1,2-propanediol which may be further purified by distilling under reduced pressure.

To further illustrate the present invention, and not by way of limitation, the following examples will be given. Unless otherwise specified, all percents, ratios, parts, etc., are by weight.

EXAMPLES 1 AND 2

The pH value of a medium comprising 1% of glucose, 0.5% of peptone, 0.3% of meat extract and 0.3% of yeast extract was adjusted to 7.0. Then, 100 ml portions of the medium were introduced into 500 ml Erlenmeyer flasks and sterilized at 120° C. for 15 minutes. Then, 0.8 ml of a 25% (w/v) aqueous solution of 3-chloro-1,2-propanediol, which had been sterilized by filtering through a membrane filter, was added thereto.

Next, each strain shown in Table 1 was inoculated into each medium and cultured therein at 30° C. for 48 hours under shaking. Then, the medium was centrifuged to thereby collect cells. After washing with 100 ml of a 100 mM phosphate buffer solution once, the cells were suspended in 100 ml of a 1.0% (w/v) solution of 1,3-dichloro-2-propanol in a 1 M phosphate buffer solution (pH 7.5) and shaken at 30° C. for 22 to 23 hours.

After the completion of the reaction, the cells were removed from the reaction mixture by centrifuging. Then, the 3-chloro-1,2-propanediol thus formed in the supernatant was determined by gas chromatography so as to calculate the yield of the product from the substrate. The product in the supernatant was extracted with 50 ml portions of ethyl acetate four times and the extract was dehydrated over anhydrous sodium sulfate. After distilling off the solvent under reduced pressure, a syrup was obtained.

The specific rotation of this syrup was measured. Table 1 shows the results. The theoretical data for (R)-(—)-3-chloro-1,2-propanediol shown in the literature are as follows.

$[\alpha]_D^{22} = -6.9$ (c=2, H$_2$O)

The 3-chloro-1,2-propanediol in each syrup was tosylated in a conventional manner and the presence of the (R)-compound was examined by analysis with an optical isomer by high-performance liquid chromatography with the use of a Chiralcell (OC) column manufactured by Daicel Chemical Industries.

TABLE 1

| Example | Strain | Yield (%) | Specific Rotation $[\alpha]_D^{22}$ |
|---|---|---|---|
| 1 | N-653 | 28.7 | −5.2 |
| 2 | N-1074 | 77.2 | −5.7 |

EXAMPLE 3

The N-4701 strain was inoculated into the same medium as those used in Examples 1 and 2, and cultured therein at 30° C. under shaking for 48 hours. 80 ml of the culture medium was centrifuged to thereby collect cells. These cells were washed with 80 ml of a 100 mM tris-HCl buffer solution (pH 8.0) once and then suspended in 40 ml of a 1.0% (w/v) solution of 1,3-dichloro-2-propanol in a 1 M tris-HCl buffer solution (pH 8.0). The resultant suspension was stirred at 20° C. for 6 hours.

After completion of the reaction, the cells were removed from the reaction mixture by centrifuging. The 3-chloro-1,2-propanediol thus formed in the supernatant was determined by gas chromatography. Thus, it was found that the yield of the product based on the substrate was 100%. The product was extracted from the supernatant with 50 ml portions of ethyl acetate thrice and the extract was dehydrated over sodium sulfate. After removing the solvent under reduced pressure, a syrup was obtained.

The specific rotation of this syrup was as follows.

$[\alpha]_D^{22} = -5.05$ (c=1, $H_2O$)

The 3-chloro-1,2-propanediol in the syrup was tosylated in a conventional manner and the presence of the (R)-compound therein was examined by analysis with an optical isomer by high-performance liquid chromatography with the use of a Chiralcell (OC) column manufactured by Daicel Chemical Industries.

While the invention has been described in detail and with reference to specific embodiments thereof, it will be apparent to one skilled in the art that various changes and modifications can be made therein without departing from the spirit and scope thereof.

What is claimed is:

1. A process for the production of an optically active (R)-(−)-3-Halo-1,2-propanediol which comprises contacting a 1,3-dihalo-2-propanol with a dehalogenase originating from a microorganism.

2. A process as claimed in claim 1, wherein said microorganism belongs to the genus Corynebacterium or Microbacterium.

* * * * *